United States Patent [19]

Szabados

[11] Patent Number: 4,678,559
[45] Date of Patent: Jul. 7, 1987

[54] TEST SPECIMEN CONTAINER FOR PASTY SPECIMEN MATERIAL

[76] Inventor: Andreas Szabados, Otto-Heilmann-Strasse 2, D-8022 Gruenwald, Fed. Rep. of Germany

[21] Appl. No.: 804,348

[22] Filed: Dec. 3, 1985

[51] Int. Cl.$^4$ .................... B03B 7/00; G01N 1/28; G01N 33/48

[52] U.S. Cl. .................... 209/17; 209/173; 422/101

[58] Field of Search .............. 209/17, 173; 210/927; 422/101, 102, 99; 356/36; 435/293, 294, 296, 301, 810, 30; 220/20.5, 22; 206/229

[56] References Cited

U.S. PATENT DOCUMENTS

| 3,819,045 | 6/1974 | Greenwald .................. 209/17 |
| 4,288,316 | 9/1981 | Hennessy . |
| 4,318,803 | 3/1982 | Holmgren . |
| 4,357,249 | 11/1982 | Mehra et al. . |

FOREIGN PATENT DOCUMENTS 2835358 8/1981 Fed. Rep. of Germany .
3218079 12/1982 Fed. Rep. of Germany .
8301194 4/1983 PCT Int'l Appl. .
474060 7/1984 Switzerland .

OTHER PUBLICATIONS

Sarstedt Katalog 77/78, Veterinarmedizinische-Parasitologie (Boch).

Primary Examiner—Frank Sever
Attorney, Agent, or Firm—Toren, McGeady & Associates

[57] ABSTRACT

A sample-taking vessel 10 for pasty sample material, especially faeces, to be distributed in suspension fluid comprises a sample-taking cup 12 fitted on a vessel lid 14 and open towards the vessel bottom. The vessel bottom is formed with an elevation 28 which is shaped complementarily to the sample-taking cup 12. The cup wall 42 is provided at least in zones with sieve openings 44 out of which the sample material is forced and finely distributed in the suspension fluid 46 in the closing of the sample-taking vessel 10 with the aid of the vessel lid 14.

22 Claims, 8 Drawing Figures

U.S. Patent  Jul. 7, 1987  4,678,559
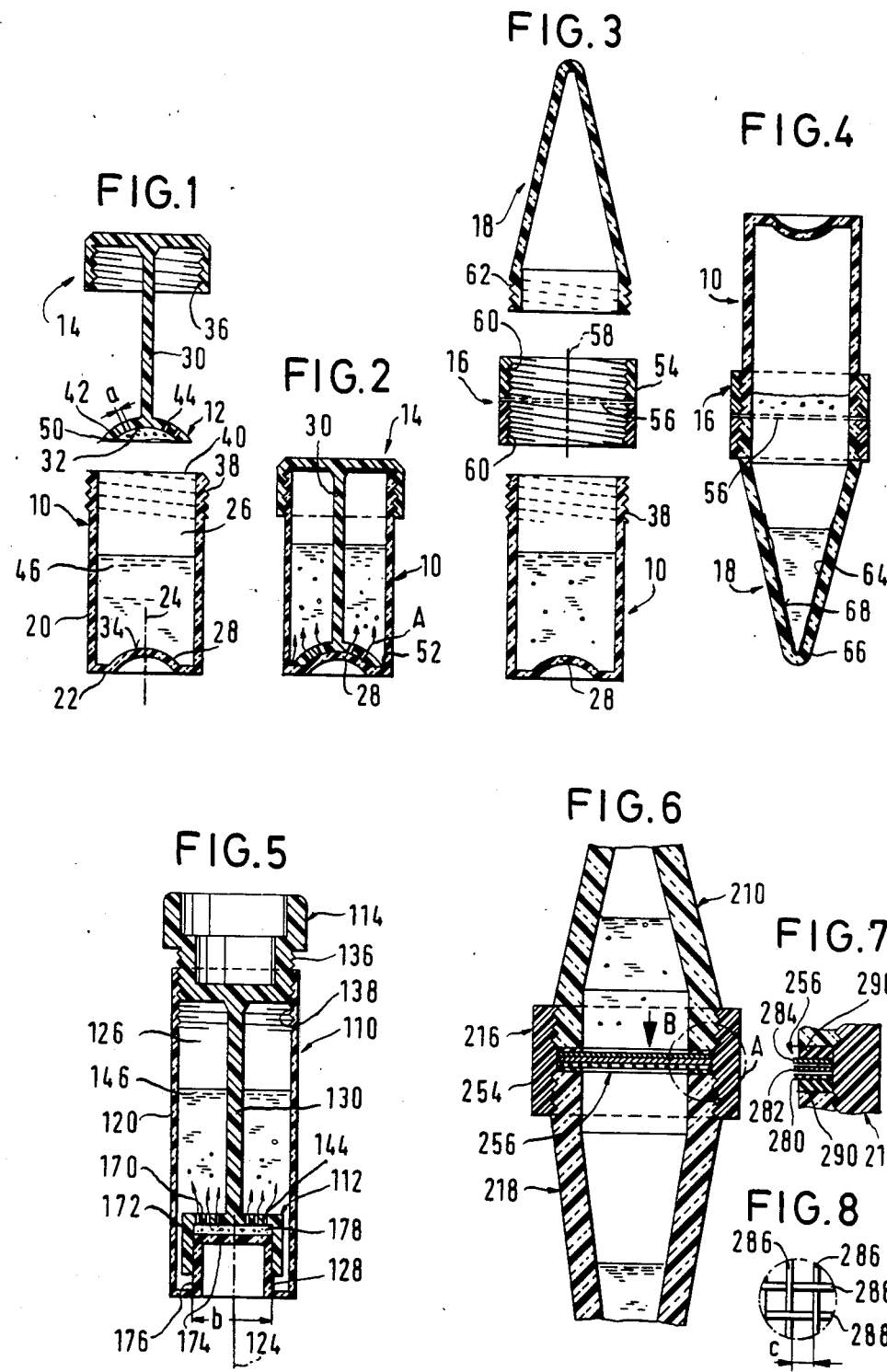

TEST SPECIMEN CONTAINER FOR PASTY SPECIMEN MATERIAL

The invention relates to a sample-taking vessel for pasty sample material, especially faeces, to be distributed in fluid, especially suspension fluid, with a sample-taking cup fitted on a vessel lid, open towards the bottom of the vessel, in the interior of the vessel.

A sample-taking vessel of this kind is known (for example Saarstedt Catalogue 77/78 W. Saarstedt, Rommelsdorf, 5523 Nümbrecht). The sample-taking cup consists of a scoop fitted on the vessel lid. If with such a sample-taking vessel it is desired to obtain a fine distribution of the pasty sample material in the suspension fluid, a stirring around of the scoop in the interior of the vessel is indicated. However thus in many cases it is not possible to obtain a sufficiently fine distribution of the sample material in the fluid. The stirring around means an additional operation which moreover is unpleasant in the case of faeces samples.

The problem of the invention consists in preparing a sample-taking vessel which with extremely simple handling ensures a very good distribution of the sample material in the fluid.

The problem is solved in that the cup wall is provided with sieve openings, at least in zones, of which the upper side facing the interior of the vessel is shaped so as substantially to match the inner side of the cup, and in that the inner side of the cup, when the vessel is closed lies with substantially entire surface against the upper side of the elevation. Accordingly when the vessel lid is set upon the sample-taking vessel the sample material situated in the sample-taking cup is positively forced through the sieve openings into the suspension fluid; according to the number and dimensions of the sieve openings a fine distribution of the sample material in the suspension fluid results. The sample material is brought into the suspension fluid without noticeable losses, since the elevation fills out the cup completely after the manner of a plunger. Consequently the possibility exists of quantitative evaluations, since the sample-taking cup is suitable for the reception of a defined sample volume.

In further development of the invention it is proposed that the sieve opening edges of the cup wall on the elevation side are sharp-edged. In this way the comminution effect of the sieve openings in the pressing of the sample material through the sieve openings is reinforced. In this way sample particles which are too large for the subsequent measurements are reliably comminuted, which is not achieved in many cases by the conventional stirring.

In the case of faeces samples the sieve openings have for preference a clear internal width of about 0.5 to 2 mm., preferably about 1 mm.

In order that in the case of larger but non-comminutable particles the sample-taking vessel may nevertheless be closed, it is proposed that the sample-taking cup is retained on the lid yieldably in the direction towards the lid. Alternatively or additionally the cup wall and/or the elevation can be made yieldable. These parts can be plastically or elastically yieldable, but elastic yieldability is preferred at least in the case of multiple use of the vessel. Since the sample-taking vessel with vessel lid can be produced at favourable cost, by reason of its simple form, in general however the sample-taking vessel will be used as a disposable article.

The desired elastic yieldability with low production costs is preferably achieved in that the fitting for the sample-taking cup on the vessel lid and/or the cup wall and/or the elevation is or are formed with polyethylene. In this case the retaining fitting is preferably of stem form.

In a first, especially simple form of embodiment of the invention the cup wall is of substantially part-spherical curvature.

In an alternative form of embodiment thereto the cup wall is formed by a cup bottom provided with the sieve openings and a substantially hollow-cylindrical cup side wall starting from the cup bottom. This form of embodiment, which resembles a piston-cylinder arrangement, ensures even in the case of relatively large sample volumes that practically the whole volume of the sample is forced out of the cup into the suspension fluid.

In order to avoid lateral escape of sample material between vessel bottom and cup wall circumferential edge without simultaneous comminution and fine distribution of this sample material into the suspension fluid, it is proposed that the circumferential edge of the cup wall rests in substantially sealing manner on the elevation and/or the vessel side wall, namely at the latest when in the setting of the vessel lid upon the sample-taking vessel the elevation penetrates into the sample-taking cup. Then the whole of the sample material is forced exclusively through the sieve openings. It is however also possible to provide between the circumferential edge of the cup wall and the elevation or the vessel side wall a distance which does not substantially exceed the clear internal width of the sieve openings.

In many methods of examination it is necessary to filter the suspension. Hitherto the manner of execution of this was that the suspension was poured out of the sample-taking vessel into a filter funnel set upon a filtrate vessel. This measure is unpleasant for the person concerned in the case of faeces samples, and in the case of infectious material it is not without danger under some circumstances. In accordance with the invention now a filter body provided with a filtrate vessel is used which can be placed upon the sample-taking vessel in place of the vessel lid.

The connection of the filter body and the sample-taking vessel becomes especially simple, without special constructional precautions on the sample-taking vessel, if the filter body is connectable, usually screwable, with the sample-taking vessel in the same way as the vessel lid. The same style of fastening is preferably also used for the connection of filtrate vessel and filter body, in order to facilitate handling.

In one form of embodiment of the invention which is distinguished by especially simple construction the filter body comprises a substantially hollow-cylindrical filter carrier in the passage of which, at a distance from both passage ends, a single-layer or multi-layer filter is provided. In this case in the direction of the axis of the hollow cylinder a screw threading for the connection of the filter body with the sample-taking vessel and the filtrate vessel is provided on each of the two sides of the filter.

Especially low production costs for the filter body result if the filter carrier is formed by two screw rings, each provided with one of the screw threadings, which are secured, preferably by adhesion, to one another in the region of the filter.

In order to preclude tearing of the filter, especially in centrifuging, it is proposed that the filter body comprises a support sieve on the side of which facing the sample-taking vessel a main filter is arranged. In order to prevent premature blockage of the main filter by larger particles it is proposed additionally to use a pre-filter.

It is proposed that the support sieve, the main filter and/or the pre-filter be formed by a metal or synthetic plastics sieve. Such filters have high mechanical stability and are inert to most of the fluids coming under consideration. The use of a fabric sieve in each case is especially preferred, since the sieve openings formed between the fabric threads possess fairly precisely defined aperture dimensions. Thus it is ensured that particles as from a specific particle size are retained, but particles of smaller size are let through. The objects which are important for an examination, perhaps parasite diagnosis, are reliably situated on the desired side of the filter (on the filter or in the filtrate as the case may be) after the filtration. With the cotton or paper filters usual hitherto this sharpness of filter separation does not exist however by reason of the irregularity of the fibres and their adhesion capacity in relation to some particles.

An O-ring is used in each case for sealing the filter body in relation to the sample-taking vessel and the filtrate vessel.

In the case of a series of examination methods a stratification of specific fluids one above the other results within the sample-taking vessel and/or the filtrate vessel. Frequently only the lowermost stratum is of interest. Since this often is only of small volume, to facilitate the isolation of this fluid the vessel concerned is made approximately pointedly tapering towards the vessel bottom. If now the upper non-interesting strata are poured away by appropriate tilting of the vessel to the horizontal, then frequently the interesting lowest stratum also escapes from the vessel. In order to prevent this or at least make it difficult it is proposed that the inner wall of the vessel, at least in the region of the tip, be roughened and/or provided with a coating, preferably silicate coating, which improves the adhesion of the sample material or the filtrate to the inner wall of the vessel.

The invention is also concerned with a sample-taking vessel with an agitator insert for the mixing of fluids or of fluids and solids in general. In order to ensure an intensive mixing with low constructional expense and very simple handling, without the danger of splashing or the like, it is proposed that the agitator insert is movable up and down in the sample-taking vessel and is provided with a turbulence-inducing element substantially of plate form provided with a passage opening and substantially filling out the cross-section of the vessel (perpendicularly of the direction of movement). It has appeared that in the case of this style of mixing the liquid surface remains approximately at rest, so that splashing is precluded. The turbulence leads rapidly and reliably to the desired intensive mixing. In the case of the sample-taking vessel as initially described the turbulence-inducing element is formed by the sample cup provided with the sieve openings.

The invention further relates to a method for processing pasty sample material, especially infectious material such for example as faeces, with the aid of the sample-taking vessel as described above, wherein the sample (a) is suspended in a first fluid, possibly fixing solution, especially MIFC solution;
(b) is filtered and
(c) the filtrate may be centrifuged.

A method of this kind is known (Josef Boch, Rudolf Supperer "Veterinary-medical Parasitology", Verlag Paul Parey, Berlin and Hamburg, 1983). In this case the faeces sample is taken up with the aid of the sample-taking cup of scoop form and put into the otherwise empty sample-taking vessel. Then the sample-taking vessel is sent to the laboratory and there opened and the faeces sample is put into a vessel containing the first fluid and intensively mixed with an electric agitator. With the aid of a pipette a sample volume is taken from the suspension and poured into a filter funnel, containing a gauze, above a filtrate vessel. The filtrate vessel may be centrifuged.

Thus the unpleasant, possibly infectious sample or sample solution is moved several times by hand from one vessel into another.

In order, compared therewith, to make the carrying out of the method much simpler and less unpleasant for the persons concerned it is proposed that at the sample-taking site the first fluid is charged into the sample-taking vessel before the sample is added, in the laboratory the vessel lid is removed and in its place the filter body with filtrate vessel is fitted on the sample-taking vessel, the sample-taking vessel is turned through 180° about a horizontal axis and the sample is filtered, possibly with assistance from manual shaking, and if necessary the filtrate vessel is put into a centrifuge. Since according to the invention the sample is distributed in the first fluid immediately after taking, an instantaneous fixing of the sample material results so that decomposition of the interesting particles prior to laboratory treatment is suppressed. Moreover at the same time smell generation and the development of gases which could result in explosion of the sample-taking vessel during transport are suppressed. When the above-described sample lid with perforated sample-taking cup is used the closure of the sample-taking vessel immediately positively causes a certain suspension of the sample within the first fluid. It is here ensured that the suspended sample particles do not exceed a specific size, so that the danger of resinification existing in the case of larger particles is precluded. Pouring on of suspension fluid, which is very unpleasant by reason of the immediate visual contact with the faeces-containing solution, is avoided. The sample fluid remains in the sample-taking vessel until the filter body is set thereon; for filtering it is merely necessary for the sample-taking vessel, fitted with the filter body, to be turned through 180° about a horizontal axis and then shaken. If centrifuging is desired for this purpose the filtrate vessel can be put directly into the centrifuge. The subsequent examination of the fluids in the filtrate vessel and of the particles retained in the filter no longer involves unpleasant impressions for the corresponding person.

The stated method for processing pasty material, especially faeces, can be carried out with particular advantage with the sample-taking vessel formed in accordance with the invention as described in greater detail at the outset, especially because the perforated sample-taking cup ensures a reliable fine distribution and if necessary comminution of the pasty material. Moreover again within the sample-taking vessel an intensive mixing can be achieved, especially in the laboratory before filtration, namely due to the fact that the sample-taking cup is moved repeatedly up and down in the interior of the vessel by appropriate handling of the vessel lid. Apart from this simple handling the advantage is obtained that no aids (cotton wool sticks) which may even under some circumstances have to be sterilised are necessary for the initial stirring-in and subsequent intensive mixing. The taking of the sample can be effected directly with the aid of the sample cup. Finally contamination of the environment need not be feared either in the initial suspension of the sample in the first fluid or in subsequent mixing. A closed processing system results in which the stressing of the operators (contamination, solvent vapours) is reduced to a minimum compared with the formerly usual "open" processing methods. The reliability of the method is also increased by the intensive mixing. Finally by reason of the use of metal or synthetic plastics fabric filters a sharp separation of the particles according to their size results. For filtering out parasites in the faeces a fabric will be used with a clear mesh width between 150 and 300 μm, preferably 180 to 220 μm, optimally about 200 μm. The filter then reliably retains parts which are larger than the parasites to be examined. By reason of the fact that, compared with gauze or paper filters, the adhesion of the parasites to the filter material is clearly reduced, in some cases even negligible, even low parasite densities can reliably be substantiated. Except for microscopic diagnosis, all working steps can be carried out by hand without burdening or endangering the environment. The manual actions are simple and little space is needed, so that large series examinations (screening) are readily possible.

The combination of the sample-taking vessel, usable as transport, processing and storage vessel, with the attachable filter body with filtrate vessel can be used, independently of the above-stated MIFC technique and independently of the configuration of the vessel lid with perforated sample-taking cup, in general for the filtration of suspensions especially those containing bacteria, viruses, antigens, enzymes or substrata. Simple handling without burdening the operator (splashes, solvent vapours) is guaranteed according to the invention in that the suspension is charged into the sample-taking vessel, the filter body with filtrate vessel if fitted and, after this arrangement has been turned through 180° about a horizontal axis, filtration is effected, possibly with assistance of manual shaking or by insertion into a centrifuge. By reason of the defined pore size of the fabric filter (synthetic plastics material or metal) the desired particle sizes can be sharply separated from one another. For the separation of bacteria and viruses (or virus particles) a mesh width between 0.15 and 0.45 especially, optimally about 0.2 μm., is selected.

From PCT-A-W083/01194 it is known to fit on the vessel lid both a sieve which substantially fills out the vessel cross-section and a sample-taking cup, open towards the bottom of the vessel, with openings in the cup wall. The sample-taking cup is fitted on the sieve through a retaining fitting.

In contrast thereto, one aim of the invention consists in preparing a sample-taking vessel of this kind which, with the simplest handling, ensures a very good distribution of the sample material in the fluid. The sample-taking cup formed in accordance with claim 24 has, in addition to the function of sample collecting, also that of fine, complete distribution of the sample material in the fluid. This is achieved firstly in that in the screwing shut of the vessel the pasty sample material is forced practically completely out of the sample-taking cup, namely in fine jets corresponding in cross-section to the sieve opening width, while according to the nature of the pasty sample material a comminution of larger material particles is also effected by the sieve. These material sample flow filaments above the sieve with correspondingly large flow filament surface essential for the mixing already form a relatively fine sample material distribution within the fluid. For further improvement of the distribution moreover the sieve formed by the cup wall can be moved up and down within the fluid by appropriate upward and downward movement of the vessel lid, whereby again the mixture of sample material and suspension fluid moves in the form of fine flow filaments through the individual sieve openings and through the annular gap, with the result of an intensive, uniform fine intermixing of the sample material with the suspension fluid. By reason of the incompressibility of the fluid and the fineness of the flow filaments and of the eddies the fluid surface remains practically completely still in the raising and lowering of the vessel lid. The danger of contamination of the environment by splashes is negligible.

U.S. Pat. No. 4,032,437 shows a sample-taking vessel with a vessel lid and a vessel bottom with sample-taking cup open towards the vessel lid. In contrast to the sample-taking vessel according to the classification with sample-taking cup retained on the vessel lid and correspondingly simple sample-taking without accessories, in the case of the sample-taking vessel according to the U.S. patent the pasty sample material must be scraped with the aid of a separate spatula or the like into the sample-taking cup, which makes the handling more difficult and in the case of faeces substantially increases the unpleasantness of sample-taking by the patient. A piston provided with sieve openings with stem mounting can be introduced, independently of the lid, into the vessel, but only as far as the upper edge of the sample-taking cup. The pasty sample material within the sample-taking cup therefore cannot be reached by the piston at all, so that in contrast to the invention the pasty sample material cannot be forced at all by depression of the sieve-type piston out of the sample-taking cup into the vessel interior above the sieve-type piston for the mixing of the suspension fluid. The piston according to the U.S. patent is fitted with sliding fit into the vessel, whereas in the case of the invention an annular gap is provided between the circumferential edge of the cup wall and the vessel side wall, at least in the region of the elevation, additionally ensuring intensive mixing. Finally by reason of the retention of the cup wall on the lid in accordance with the invention firstly a reduction of the number of necessary components and also an increase of reliability in handling result, since the expulsion of the pasty sample material from the taking cup and intermixing with the suspension fluid take place automatically on closing of the lid and subsequent reopening of the lid.

From Fed. German No. A-3,218,079 a rotor within a cup is known which by rotation at sufficiently high speed breaks up cell accumulations in the region between rotor and cup with the aid of appropriate shear forces. The clear distance between rotor and cup amounts to 4 mm. In the invention on the other hand intermixing is achieved by axial displacement of the sample-taking cup, provided with sieve openings, within the vessel.

The invention will be explained below by preferred examples of embodiment with reference to the drawing, wherein:

FIG. 1 shows a lateral sectional view of a first form of embodiment in accordance with the invention of a sample-taking vessel before the fitting of the vessel lid;

FIG. 2 shows the arrangement according to FIG. 1 with vessel lid fitted;

FIG. 3 shows the sample-taking vessel according to FIGS. 1 and 2 before the fitting of a filter body and a filtrate vessel;

FIG. 4 shows the sample-taking vessel according to FIG. 3 provided with the filter body and the filtrate vessel and used for filtering;

FIG. 5 shows a lateral sectional view of a second form of embodiment of a sample-taking vessel with partly screwed-in vessel lid;

FIG. 6 shows a filtering arrangement similar to FIG. 4;

FIG. 7 shows the detail A in FIG. 6 and

FIG. 8 shows an enlarged detail of a filter fabric used in the arrangement according to FIGS. 6 and 7 (seen in the direction B in FIG. 6).

The sample-taking vessel 10 as represented in FIGS. 1 to 4 can be used according to choice with a vessel lid 14 having a sample-taking cup 12, as visible in FIGS. 1 and 2, or, without the necessity of transferring the vessel contents, with a filter body 16 for the filtration of the vessel contents according to FIGS. 3 and 4. The sample-taking vessel 10 comprises a hollow-cylindrical vessel side wall 20 and a vessel bottom 22. The vessel bottom 22 is shaped with a convex (seen from the vessel interior 26), substantially part-spherically shaped elevation 28 arranged centrally in relation to the vessel axis 24. The sample-taking cup 12, connected through a stem 30 with the vessel lid 14, is domed to match the elevation 28. Now the length of the stem 30 is fixed so that when the vessel lid 14 is screwed on completely according to FIG. 2 the inner side 32 of the cup rests with full surface on the upper side 34 of the elevation 28. The approximately hat-shaped lid 14 is provided with an internal threading 36 which can be screwed on to an external threading 38 of the cup side wall 20 in the region of the cup opening 40.

The cup wall 42 of the sample-taking cup 12 is provided in distribution over the entire wall with sieve openings 44 with a clear internal width a between 0.5 and 2 mm. optimally about 1 mm.

For the taking of a sample either the sample is scraped with the aid of a spatula or the like into the sample-taking cup 12 or the sample is taken directly with the aid of the sample-taking cup. As the volume of the sample-taking cup is predetermined, quantitative measurements can also be executed. Previously a first fluid 46 serving as fixing and/or transport medium has been charged into the sample-taking vessel 10. In the case where the MIFC technique is used the first fluid consists of formalin-water-glycerine plus merthiolate (Thimerosal).

The vessel lid 14 is set with the sample-taking cup 12 foremost upon the sample-taking vessel 10 and screwed thereto. During this screwing action the cup wall 42 increasingly approaches the elevation 28. Between the wall 20 of the vessel and the circumferential edge 50 of the cup wall 42 a narrow annular gap 52 is formed having a gap width not exceeding the value a. By reason of this annular gap in the downward movement of the sample-taking cup 12 within the sample-taking vessel 10 the first fluid 46 can readily escape upwards past the circumferential edge 50. However as soon as the sample material 32 reaches the cup bottom 22 and the sample-taking cup 12 is moved further downwards (by reason of the screwing-on movement of the vessel lid 14), it is compressed and forced out of the sieve openings 44 and the annular gap 52 indicated in FIG. 2. In FIG. 2 corresponding small flow arrows are designated by A. According to the sieve opening width a and the number of sieve openings a plurality of fine sample material flow filaments (jets) into the first fluid results.

This leads to a fine distribution of the sample material in the first fluid 46. Sample material particles which are larger than the sieve opening width a are if possible crushed between the two parts—elevation 28 and cup wall 42—which press against one another like plungers, so that finally they can escape through the sieve openings 44. Those particles which are not crushable, by reason of their hardness, remain between cup wall 42 and elevation 28. So that the vessel lid 14 can nevertheless be screwed on completely and thus seals the sample-taking vessel, both the cup wall 42 and the stem 30 are made elastically yieldable. This is achieved by manufacture of these parts from polyethylene. Alternatively or additionally the elevation 28 can also be made elastically yieldable.

Thus the fine distribution of the sample material in the first fluid 46 is achieved solely by the screwing shut of the vessel lid 14. The suspension of the sample material in the first fluid 46 can be further reinforced by slight subsequent shaking. If necessary the degree of suspension can be further increased in a simple manner, in the sample-taking or subsequently in the laboratory, by moving the sample-taking cup 12 up and down within the sample-taking vessel by raising and lowering the vessel lid 14. An intensive mixing occurs by reason of the eddy formation in the region of the sieve openings 44 and of the annular gap 52. No additional stirring appliances, which might have to be sterilised separately, are required. The danger of contamination of the environment by splashes or solvent vapours is greatly reduced.

The sample-taking vessel 10 can be used directly as transport vessel between sample-taking site and laboratory. The first fluid 46 prevents fermenting of the sample material, so that explosion of the sample-taking vessel cannot occur. Furthermore the first fluid 46 also suppresses smell generation in the case of corresponding sample material. Finally the first fluid can also ensure sterilisation and fixing of the sample material.

In the laboratory the vessel lid 14 is removed, a second fluid, especially organic solvent (ether or ethyle acetate) or dyestuff (for example Lugol's solution) may be added and intensive mixing is again effected by movement of the sample-taking cup up and down. Now for the subsequent filtration the filter body 16 visible in FIGS. 3 and 4 is screwed on. The filter body 16 comprises a hollow-cylindrical filter carrier 54 in the passage of which a single-layer or multi-layer filter 56 is provided at a distance from both passage ends. On both sides of the filter 56, in the direction of the axis 58 of the hollow cylinder there is provided in each case a screw-in threading 60 for the connection of the filter body 16 with the sample-taking vessel (external threading 38) and the filtrate vessel 18 (external threading 62). Thus the filtrate vessel 18 can be screwed to the filter body 16 before or after the filter body 16 is screwed on to the sample-taking vessel 10. The filter carrier 16 can be produced in an especially simple manner in that two screw rings each provided with the screw-in threading 60 are stuck with their end faces to one another with interposition of the filter 56. A special filter construction will be described in greater detail below with reference to FIGS. 6 to 8.

After the parts 10, 16 and 18 have been screwed together the arrangement is turned through 180° about a horizontal axis into the position according to FIG. 4. If now in the case of the MIFC method of parasite identification the arrangement is shaken in the vertical direction (about 15 seconds), then about half of the suspension is obtained as filtrate in the filtrate vessel 18. The filtration of the remaining suspension is achieved in a simple manner in that the upper end of the arrangement (that is the sample-taking vessel 10) is grasped and shaken two or three times while directed downwards (as in shaking back a medical mercury thermometer). Now the whole of the filtered suspension is situated in the filtrate vessel 18. Now the sample-taking vessel 10, serving as despatch vessel, can be removed; the particles deposited on the filter 56 can be examined separately. The filtered suspension in the filtrate vessel 18 can now be submitted to appropriate examination. In the case of the MIFC method for parasitology the suspension is left to stand for about 12 to 24 hours, if no centrifuge is available. If a centrifuge is available the filtrate vessel 18 can be placed immediately in the centrifuge and centrifuged. In both cases then one obtains a liquid stratification in the filtrate vessel 18. In the case of the MIFC method only the lowermost stratum within the downwardly conically tapering filtrate vessel 18 is of interest. The strata lying thereabove are decanted carefully. In order to prevent, or at least make more difficult, an escape by oversight of the interesting lowermost stratum in this operation, the inner side 64 of the vessel is roughened and/or provided with a coating improving the adhesion of the sample material or filtrate to the vessel inner side 64, at least in the region of the tip 66. A silicate coating 68 has proved itself especially well.

The remaining lowermost stratum is now examined in more detail. For this purpose a drop of this stratum is put on to a slide, a glass cover is applied and microscopic examination is effected.

In the case of the second form of embodiment of a sample-taking vessel as represented in FIG. 5 those components which correspond in function to those of the form of embodiment according to FIGS. 1 to 4 are provided with the same reference numerals, increased in each case by the FIG. 100. The sample-taking vessel accordingly designated by 110 is provided, in departure from the first form of embodiment, with an internal threading 138 into which a vessel lid 114, accordingly provided with an external threading 136, can be screwed. The main difference from the first form of embodiment lies however in the different configuration of the sample-taking cup 112 and accordingly of the elevation 128. The sample-taking cup is provided with a circular cup bottom 170 radial in relation to the vessel axis 124, in which bottom the sieve openings 144 are formed. From the circumferential edge of the cup bottom 170 a hollow-cylindrical cup side wall 172 issues. The elevation 128, shaped complementarily thereto, accordingly comprises an elevation bottom 174 and a hollow-cylindrical elevation side wall 176, the external diameter b of which corresponds approximately to the internal diameter of the cup side wall 172. Between the external circumference of the cup side wall 172 and the internal circumference of the vessel side wall 120 there is a sufficiently large gap, for example of about 1.5 mm., for the overflowing of the fluid 146 in the pushing downwards of the sample-taking cup 112. The sample-containing space 178 enclosed by the cup bottom and the cup side wall 172 is consequently cylindrical. In the pushing of the sample-taking cup 112 into the sample-taking vessel 110 finally the cup side wall 172 comes into contact with the elevation side wall 176. Then the elevation 128 travels after the style of a piston into the sample-taking cup 112 and displaces the sample material within the sample-containing space 178. This is forced in jet manner through the sieve openings 144 into the first fluid 146. When the lid 114 is screwed on fully the cup bottom 170 lies with full surface on the elevation bottom 174, unless particles, for example small stones, hold the cup bottom at a corresponding distance from the elevation bottom. Since the stem 130 is elastically yieldable, the vessel lid 114 can nevertheless be screwed on in completely sealing manner.

To improve the distribution of the sample material in the fluid within the sample-taking vessel 110 it is possible, as already described with reference to FIGS. 1 and 2, to push the sample-taking cup 112 up and down several times within the interior 126 of the vessel.

In a form of embodiment of the invention which is not illustrated the stem carrying the sample-taking cup is detachably connected with the vessel lid, for which purpose the vessel lid may be correspondingly provided on its inner side with a blind hole for insertion.

The more precise construction of the sieve appears from FIGS. 6 to 8. Components which correspond in function to those in FIGS. 1 to 3 are provided with the same reference numerals, in each case increased by the number 200. The sample-taking cup 210 is screwed from one side and the filtrate vessel 218 from the other side into the filter carrier 216. In the example of embodiment now to be described filtrate vessel 218 and sample-taking vessel 210 have the same pointedly tapering form, since the filtration according to the invention can be carried out within a closed system even independently of the sample suspension with the aid of appropriately formed sample-taking vessel and vessel lid (elevation and sample-taking cup), although, especially in the MIFC technique, it can be carried out with special advantage with a sample-taking vessel formed accordingly.

The filter 256 is in three layers in all. A support sieve 280 is followed by a main filter 282 and then a prefilter 284. At least one of the layers, optimally all the layers, is or are formed by a fabric sieve, that is a sieve with fabric threads or strands crossing one another in the manner of woven fabric. In FIG. 8 there are shown first threads 286 lying parallel to one another and crossing at right angles with second threads 288. The clear mesh width c between successive threads is fixed according to the respective layer (support sieve or main filter or pre-filter) and the desired particle size which is just to be let through. Thus for example for filtering out bacteria, viruses, enzymes and substrata from larger parasites the following mesh widths will be selected support sieve 20–100 $\mu$m, main filter 3–5 $\mu$m, pre-filter 20–100 $\mu$m. For the filtration of bacteria and fungus spores from larger particles the following values are selected for the clear mesh width c: support sieve 20–100 $\mu$m, main filter 0.15–0.45 $\mu$m, pre-filter 5–20 $\mu$m.

The fabric threads formed from metal and/or synthetic plastics threads or strands prevent particles which per se ought to pass the filter from adhering to the filter. The fabric structure also results in a high sharpness of separation (low straying of the clear mesh width in a fabric sieve).

In order to hold the three layers 280 to 284 together and also to prevent escape of fluid out of the screwed-together arrangement of the parts 210, 216, 218, an O-ring 290 having according to FIG. 7 a rectangular cross-section is inserted on each of the two sides of the three-layered filter 265. With its external circumference each ring 290 rests on the inner circumference of the hollow-cylindrical filter carrier 254. The filtrate vessel 218 and the sample-taking vessel 210 press upon the end faces in each case remote from the three-layered filter 256. The multi-part filter 265 can be made exchangeable so that a filter carrier 216 may be adapted by appropriate filter selection to the various ranges of use.

The handling of the arrangement according to FIG. 6 corresponds to that of the arrangement according to FIGS. 3 and 4. Thus the filter carrier 216 with filtrate vessel 218 is to be screwed on to the sample-taking vessel 210 containing the suspension to be filtered, and then turned through 180° about a horizontal axis. The subsequent filtration can be promoted by shaking, knocking or centrifuging of the arrangement according to FIG. 6. As the system is completely closed the danger of contamination (splashes, solvent vapours or the like) is eliminated. All smell burden is also eliminated. The processing of materials which instigate unpleasant sensations, as for example faeces samples, becomes substantially more pleasant in the stated manner.

The filtering arrangement according to the invention is suitable for the rapid cleaning or sterile filtration of all liquid suspensions or solvents, and no appreciable losses of sample material occur. The processing vessel, transport vessel or storage vessel can be used directly for the filtering arrangement according to the invention, since only the filter carrier with filtrate vessel has to be set on in the usual manner, for example by screwing. The filtration method is suitable for use in delicate chromatography systems, such for example as HPLC, in the fields of immunology, molecular biology, cellular biology, bacteriology, virology or the like.

I claim:

1. Sample-taking vessel for pasty sample material to be distributed in a suspension fluid within said vessel (10), said vessel including a vessel body having an open end (40) and a closed end (22) spaced from the open end and a first direction extending between the open and closed ends and including a vessel side wall (20) extending between the open end and the closed end in the first direction, and a vessel lid (14) for closing the open end, a sample-taking cup (12), said cup extending transversely of the first direction of said vessel and substantially filling the cross-section of said vessel transversely of the first direction, said cup (12) comprising a cup wall (42) extending transversely of the first direction with sieve openings (44) extending therethrough with the width of the openings being in the range of 0.5 to 2 mm, a stem extends in the first direction between and connects said cup and said vessel lid, said cup having an interior formed by an inner side (32) facing toward the closed end of said vessel, an elevation (28) formed in the closed end of said vessel and projecting into said vessel in the first direction toward the open end, said elevation having a surface (34) facing toward the open end substantially complementary to the inner side of said cup, said cup having an outer side opposite said inner side and facing toward the open end of said vessel said inner side being arranged to seat over its full surface in contact with the surface of said elevation when said vessel lid closes the open end of said vessel, said cup having a circumferential edge (50) spaced inwardly from said vessel side wall (20) and forming with said vessel side wall an annular gap (52) having a width not greater than the width of the sieve openings in said cup wall.

2. Sample-taking vessel, as set forth in claim 1, wherein the edges of said sieve openings in said cup wall (42) on the inner side (32) thereof being sharp-edged.

3. Sample-taking vessel, as set forth in claim 1, wherein said sieve openings have a clear width (a) of approximately 1 mm for use with faeces specimens.

4. Sample-taking vessel, as set forth in claim 1, wherein said stem (30) flexibly connects said cup (12) to said vessel lid (14).

5. Sample-taking vessel, as set-forth in claim 4, wherein said stem (30) is stalk-shaped and is formed of polyethlene.

6. Sample-taking vessel, as set forth in claim 5, wherein at least one of said cup wall and elevation are formed of polyethylene.

7. Sample-taking vessel, as set forth in claim 1, wherein at least one of said cup wall (42) and said elevation (28) is flexible.

8. Sample-taking vessel, as set forth in claim 1, wherein said cup wall is spherically shaped.

9. Sample-taking vessel, as set forth in claim 1, wherein said cup wall includes a cup bottom (170) containing said sieve openings (144) and a cylindrically shaped side wall (172) extending from said bottom toward the closed end of said vessel.

10. Sample-taking vessel, as set forth in claim 9, wherein the inside of said cup side wall (172) is spaced radially outwardly from said elevation (128) by a dimension not exceeding the width of said sieve openings (144).

11. Sample-taking vessel, as set forth in claim 1, including a filter body (16), a filtrate vessel (18) secured to said filter body (16) and said filter body being engageable with said vessel at the open end thereof for receiving samples from within said vessel.

12. Sample-taking vessel, as set forth in claim 11, wherein said filter body (16) is arranged to replace and is connectible with said vessel in the same manner as said vessel lid (14).

13. Sample-taking vessel, as set forth in claim 12, wherein said filtrate vessel (18) is connectible with said filter body (16) in the same manner as said vessel lid (14).

14. Sample-taking vessel, as set forth in claim 11, wherein said filter body (16) comprises a hollow cylindrically shaped filter carrier (54) forming a passage, at least a single layer filter (56) secured within the passage and spaced from the opposite ends of the passage, said filter carrier having a screw thread on each of the opposite ends thereof for connecting said filter body to said vessel (10) and said filtrate vessel (18).

15. Sample-taking vessel, as set forth in claim 14, wherein said filter carrier comprises a pair of threaded ring-like members each having a screw thread thereon with said filter (56) secured between said ring-like members.

16. Sample-taking vessel, as set forth in claim 11, wherein said filter body (216) supports said filter made up of a support sieve (280) facing said vessel (210), a main filter on the side of said support sieve remote from said vessel, and a pre-filter (284) located on the opposite side of said main filter from said support sieve.

17. Sample-taking vessel, as set forth in claim 16, wherein at least one of said support sieve (280), main filter (282) and pre-filter (284) are formed of a metal sieve.

18. Sample-taking vessel, as set forth in claim 16, wherein at least one of said support sieve (280), main filter (282) and pre-filter (284) are formed of a plastics sieve.

19. Sample-taking vessel, as set forth in claim 11, wherein at least one O-ring (290) forms a seal between said filter body (216) and said vessel (210).

20. Sample-taking vessel, as set forth in claim 11, wherein at least one O-ring (290) forms a seal between said filter body (216) and filtrate vessel (218).

21. Sample-taking vessel, as set forth in claim 11, wherein the interior of said filtrate vessel (18) converges inwardly from said filter body (16) to the end thereof remote from said filter body and the inside surface of said filtrate vessel adjacent the end remote from said filter body is roughened.

22. Sample-taking vessel, as set forth in claim 11, wherein the inside surface of said filtrate vessel is conically shaped converging from said filter body (16) with the inside surface of said filtrate body at the end thereof spaced from said filter body being coated with a silicate coating (68) for improving the adhesion of the sample material.

* * * * *